United States Patent
Min et al.

(10) Patent No.: US 10,369,241 B2
(45) Date of Patent: Aug. 6, 2019

(54) STERILIZATION APPARATUS AND STERILIZATION METHOD USING SAME

(71) Applicant: CMTECH CO., LTD., Daegu (KR)

(72) Inventors: Heung Sik Min, Daegu (KR); Young Keun Ahn, Daegu (KR); Sung Jin Yang, Daegu (KR); Jong Wook Kim, Daegu (KR)

(73) Assignee: CMTECH CO., LTD., Daegu (KR)

( * ) Notice: Subject to any disclaimer, the term of this patent is extended or adjusted under 35 U.S.C. 154(b) by 503 days.

(21) Appl. No.: 14/902,494

(22) PCT Filed: Jun. 25, 2014

(86) PCT No.: PCT/KR2014/005660
§ 371 (c)(1),
(2) Date: Dec. 31, 2015

(87) PCT Pub. No.: WO2015/008947
PCT Pub. Date: Jan. 22, 2015

(65) Prior Publication Data
US 2016/0375167 A1    Dec. 29, 2016

(30) Foreign Application Priority Data
Jul. 15, 2013  (KR) .................. 10-2013-0082899

(51) Int. Cl.
*A61L 2/20*    (2006.01)
(52) U.S. Cl.
CPC .......... *A61L 2/208* (2013.01); *A61L 2202/11* (2013.01); *A61L 2202/122* (2013.01)

(58) Field of Classification Search
CPC ...................................................... A61L 2/208
See application file for complete search history.

(56) References Cited

U.S. PATENT DOCUMENTS 8,894,926 B2    11/2014  Hanada et al.
2007/0231201 A1    10/2007  Roberts et al.
(Continued)

FOREIGN PATENT DOCUMENTS

EP    1839679 A2    10/2007
JP    2013-081561 A    5/2013
(Continued)

OTHER PUBLICATIONS

International Search Report and Written Opinion issued in corresponding International Application No. PCT/KR2014/005660 dated Aug. 28, 2014, 7 pages.
(Continued)

*Primary Examiner* — Regina M Yoo
(74) *Attorney, Agent, or Firm* — Snyder, Clark, Lesch & Chung, LLP (57) ABSTRACT

Provided are a sterilization apparatus including a sterilization chamber, a vacuum pump connected to one side of the sterilization chamber, a vaporizer connected to another side of the sterilization chamber, and a collector having one side connected to the vaporizer and the other side connected to the sterilization chamber and a sterilization method using the sterilization apparatus. In the sterilization apparatus and the sterilization method, a hydrogen peroxide solution having a concentration of 95 wt % or higher may be obtained through multiple concentration steps and used as a sterilant, thereby considerably improving a sterilization effect.

5 Claims, 4 Drawing Sheets

(56) References Cited

U.S. PATENT DOCUMENTS

2010/0034697 A1* 2/2010 Weinberger ............... A61L 2/20
  422/28
2013/0004384 A1 1/2013 Yoo
2013/0302207 A1* 11/2013 Ahiska .................... A61L 2/208
  422/3

FOREIGN PATENT DOCUMENTS

| JP | 2013-081562 A | 5/2013 | |
|---|---|---|---|
| KR | 10-2008-0055806 A | 6/2008 | |
| KR | 10-0939788 B1 | 1/2010 | |
| KR | 10-0985801 B1 | 10/2010 | |
| WO | 2005067984 A1 | 7/2005 | |
| WO | 2007014435 A1 | 2/2007 | |
| WO | WO-2011115428 A2 * | 9/2011 | ............. A61L 2/208 |

OTHER PUBLICATIONS

Extended European Search Report issued in corresponding European Application No. 14826329.6 dated Jun. 29, 2017, 10 pages.

* cited by examiner

STERILIZATION APPARATUS AND STERILIZATION METHOD USING SAME

TECHNICAL FIELD

The invention relates to a sterilization apparatus and a sterilization method using the same, and more particularly, a sterilization apparatus capable of improving a sterilization effect by using a high-concentration sterilant aqueous solution and a sterilization method using the sterilization apparatus.

BACKGROUND ART

Medical instruments and devices are routinely sterilized by a high-pressure vapor sterilization method using water vapor saturated under a high pressure or by an ethylene oxide gas sterilization method using a chemical material such as ethylene oxide that does not cause thermal damage to tools or materials susceptible to heat.

More specifically, a high-pressure vapor sterilizer or an autoclave performs sterilization at a high temperature of about 120° C. or higher and may thus shorten the life of medical instruments and devices by causing deformation of medical appliances formed of a synthetic resin and blunting the sharp edges of medical appliances formed of steel. Particularly, expensive medical instruments and devices that are on the increase due to recent developments in surgical technology are generally susceptible to heat or moisture and are highly likely to be damaged during sterilization reprocessing. Thus, the high-pressure vapor sterilization method may not be a suitable option for such expensive medical instruments and devices.

An ethylene oxide gas sterilizer capable of minimizing thermal damage to medical instruments or devices can perform sterilization at low temperature, but requires a ventilation time of more than 12 hours after sterilization because of the possibility of any remaining ethylene oxide gas or the reaction products thereof causing carcinogenic or toxic substances. Also, the use of an ethylene oxide gas requires great care because an ethylene oxide gas is highly explosive, has been reported to serve as a genetic toxic substance causing mutations, and has even been known as a carcinogenic substance.

A sterilization method using hydrogen peroxide vapor boasts of various advantages, for example, a short sterilization time of about 30 to 60 minutes at a temperature of 40 to 50° C. and the release of harmless sterilization by-products to the human body or the environment, such as water and oxygen, and can address the shortcomings of a high-pressure vapor sterilizer and an ethylene oxide gas sterilizer.

However, during the vaporization of a hydrogen peroxide solution, which is used to produce hydrogen peroxide vapor, water evaporates and diffuses faster than hydrogen peroxide, thereby interfering with a sufficient diffusion of hydrogen peroxide. More specifically, water has a higher vapor pressure than hydrogen peroxide and thus evaporates more quickly than hydrogen peroxide. Also, since water has a smaller molecular weight than hydrogen peroxide, water vapor diffuses more quickly than hydrogen peroxide vapor.

Due to the aforementioned properties of water and hydrogen peroxide, a high concentration of water arrives at a product to be sterilized faster than hydrogen peroxide when a hydrogen peroxide solution is vaporized in the space surrounding the product.

Water vapor diffuses into a diffusion restriction space, such as a small gap (or a crevice) or a long narrow lumen, thereby suppressing the transmission of hydrogen peroxide vapor. That is, since water arrives at the product ahead of hydrogen peroxide, the product may not be able to be properly sterilized.

For an effective sterilization, it is preferable to use a highly-concentrated hydrogen peroxide solution, but in reality, it is difficult to transport, store, and handle a hydrogen peroxide solution having a concentration of 60 wt % or higher.

However, even with such numerous benefits, the sterilization method using hydrogen peroxide vapor is more limited than a high-pressure vapor sterilization method and an ethylene oxide gas sterilization method by the shape of a target object to be sterilized due to weakened diffusability of hydrogen peroxide.

In the meantime, Korean Patent Application Publication No. 10-2006-0052161 relates to a sterilization system and method and an orifice inlet control apparatus therefor, and discloses a sterilization method in which a diffusion restriction is placed into a path of evacuation of a vaporizer so as to condense hydrogen peroxide vapor while passing water vapor and the hydrogen peroxide vapor is vaporized and diffused into a sterilization chamber.

However, in the sterilization system and method of Korean Patent Application No. 10-2006-0052161, once a hydrogen peroxide solution reaches a predetermined concentration or higher, the ratio of hydrogen peroxide vapor to water vapor vaporized from the hydrogen peroxide solution becomes uniform, or increases. As a result, the concentration of the hydrogen peroxide solution no longer increases, and instead, the total amount of the hydrogen peroxide solution decreases.

Also, due to a restriction imposed by the diffusion restriction on the movement of a fluid, a higher temperature is needed to vaporize hydrogen peroxide, leading to a greater loss of a high-concentration of hydrogen peroxide. Also, since the temperature of hydrogen peroxide vapor is high, the hydrogen peroxide arrives first at the packaging material of a target object to be sterilized or a chamber structure, which has a low temperature, and condenses, thereby interfering with a rapid vaporization and diffusion.

DISCLOSURE

Technical Problems

To address the aforementioned problems, exemplary embodiments of the invention provide a sterilization apparatus and method capable of improving a sterilization effect.

Additional advantages, subjects, and features of the invention will be set forth in part in the description which follows and in part will become apparent to those having ordinary skill in the art upon examination of the following or may be learned from practice of the invention.

Technical Solutions

According to an aspect of the invention, a sterilization apparatus includes: a sterilization chamber; a vacuum pump connected to one side of the sterilization chamber; a vaporizer connected to another side of the sterilization chamber; and a collector having one side connected to the vaporizer and the other side connected to the sterilization chamber.

The sterilization apparatus may also include a vaporization valve disposed between the sterilization chamber and the collector, wherein the vaporization valve is also disposed between the sterilization chamber and the vaporizer.

The vaporization valve may have one side connected to the sterilization chamber and the other side connected in parallel between the vaporizer and the collector.

The sterilization apparatus may also include a collection valve disposed between the sterilization chamber and the collector, wherein the vaporization valve and the collection valve are connected in parallel between the sterilization chamber and the collector.

The sterilization apparatus may also include a first connecting pipe connecting the collector and the vaporization valve; a second connecting pipe connecting the vaporization valve and the sterilization chamber; a third connecting pipe connecting the collector and the collection valve; a fourth connecting pipe connecting the collection valve and the sterilization chamber; and a fifth connecting pipe connecting the vaporizer and the vaporization valve.

The first and second connecting pipes may have a larger inner diameter than the third or fourth connecting pipe and the fifth connecting pipe.

The sterilization apparatus may also include a collection valve and a fumigation valve disposed between the sterilization chamber and the collector and between the sterilization chamber and the collector, wherein the collection valve and the fumigation are connected in parallel between the sterilization chamber and the collector.

The sterilization apparatus may also include a vaporization valve disposed between the sterilization chamber and the vaporizer, wherein the vaporization valve has one side connected to the sterilization chamber and the other side connected in parallel between the vaporizer and the collector.

The sterilization apparatus may also include a first connecting pipe connecting the vaporizer and the vaporization valve; a second connecting pipe connecting the vaporization valve and the sterilization chamber; a third connecting pipe connecting the collector and the collection valve; a fourth connecting pipe connecting the collection valve and the sterilization chamber; a fifth connecting pipe connecting the collector and the fumigation valve; a sixth connecting pipe connecting the fumigation valve and the sterilization chamber; and a seventh connecting pipe connecting the vaporizer and the collector.

The fifth and seventh connecting pipes may have a larger inner diameter than the first or second connecting pipe, the third or fourth connecting pipe, and the seventh connecting pipe.

According to another aspect of the invention, a sterilization method includes: evacuating a sterilization chamber and a vaporizer; injecting an aqueous solution of a sterilant having a first concentration into the vaporizer at a first temperature and a first pressure; obtaining a sterilant aqueous solution having a second concentration by vaporizing the sterilant aqueous solution having the first concentration; injecting the sterilant aqueous solution having the second concentration into a collector at a second temperature and a second pressure; condensing sterilant vapor of the sterilant aqueous solution having the second concentration in the collector and exhausting water vapor from the collector; lowering the pressure of the sterilization chamber to a predetermined pressure and condensing a sterilant aqueous solution having the third concentration into a sterilant aqueous solution having a fourth concentration; and sterilizing a target object to be sterilized by injecting sterilant vapor of the sterilant aqueous solution having the fourth concentration into the sterilization chamber.

The sterilant may be hydrogen peroxide, and the sterilant aqueous solution may be a hydrogen peroxide solution.

The first concentration may be 60 wt %, the second concentration may be 75 wt % to 85 wt %, the third concentration may be 90 wt % to 95 wt %, and the fourth concentration may be 96 wt % or higher.

A collection valve may be disposed between the sterilization chamber and the collector, and the lowering the pressure of the sterilization chamber to the predetermined pressure and condensing the sterilant aqueous solution having the third concentration into the sterilant aqueous solution having the fourth concentration, may include repeatedly opening and closing the collection valve.

The predetermined pressure may be a pressure for sterilizing the target object in the sterilization chamber.

The injecting sterilant vapor of the sterilant aqueous solution having the fourth concentration into the sterilization chamber, may include heating the collector with temperature control means, and the heating the collector with the temperature control means, may include controlling a heating rate of the collector such that the vaporization of the sterilant is at least 80% complete before the temperature of the collector reaches the temperature of the sterilization chamber.

The first temperature in the injecting the sterilant aqueous solution having the first concentration into the vaporizer at the first temperature and the first pressure may be higher than the temperature of the sterilization chamber, and the second temperature in the injecting the sterilant aqueous solution having the second concentration into the collector at the second temperature and the second pressure may be lower than the temperature of the sterilization chamber.

Advantageous Effects

According to exemplary embodiments of the invention, a hydrogen peroxide solution having a concentration of 95 wt % or higher may be obtained through multiple concentration steps and used as a sterilant, thereby considerably improving a sterilization effect.

BEST MODES FOR CARRYING OUT THE INVENTION

Advantages and features of the invention and methods of accomplishing the same may be understood more readily by reference to the following detailed description of exemplary embodiments and the accompanying drawings. The invention may, however, be embodied in many different provides and should not be construed as being limited to the embodiments set forth herein. Rather, these embodiments are provided so that this disclosure will be thorough and complete and will fully convey the concept of the invention to those skilled in the art, and the invention will only be defined by the appended claims.

Like reference numerals refer to like elements throughout the specification. Furthermore, in the present disclosure, the expression "and/or" includes any and all combinations of the associated listed words.

In the present disclosure, expressions including ordinal numbers, such as "first" and "second," etc., may modify various elements. However, such elements are not limited by the above expressions. For example, the above expressions do not limit the sequence and/or importance of the elements. The above expressions are used merely for the purpose to distinguish an element from the other elements. For example, a first user device and a second user device indicate different user devices although both of them are user devices. For example, a first element could be termed a second element, and similarly, a second element could be also termed a first element without departing from the scope of the present disclosure.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. In an exemplary embodiment, when the device in the figures is turned over, elements described as "below" or "beneath" or "under" other elements or features would then be oriented "above" the other elements or features. Thus, the exemplary terms "below" and "under" can encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the specification and will not be interpreted in an idealized or overly formal sense unless expressly so defined herein.

Exemplary embodiments of the invention will hereinafter be described with reference to the accompanying drawings.

Figure 1A:
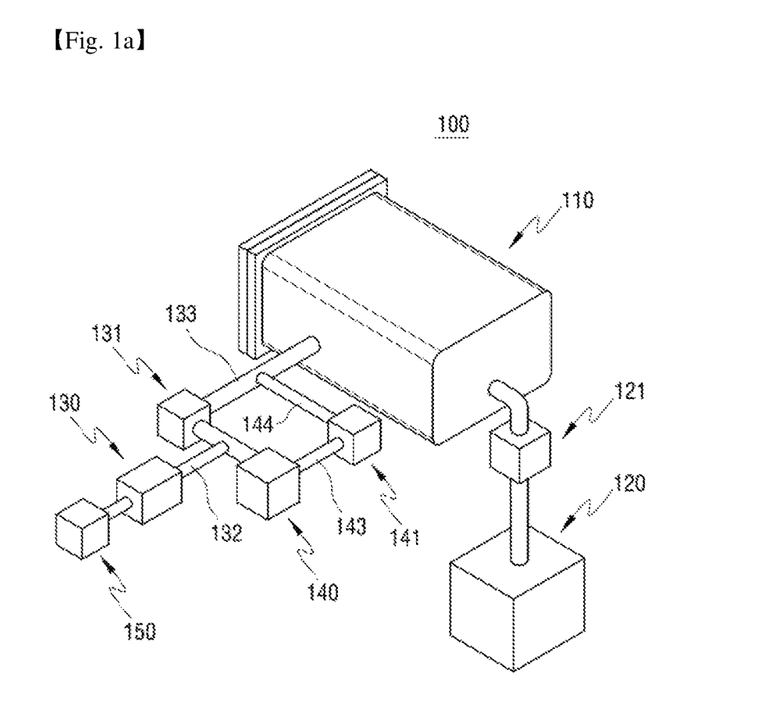
FIG. 1A is a schematic perspective view of a sterilization apparatus using a sterilant aqueous solution, according to a first exemplary embodiment of the invention.
Figure 1B:
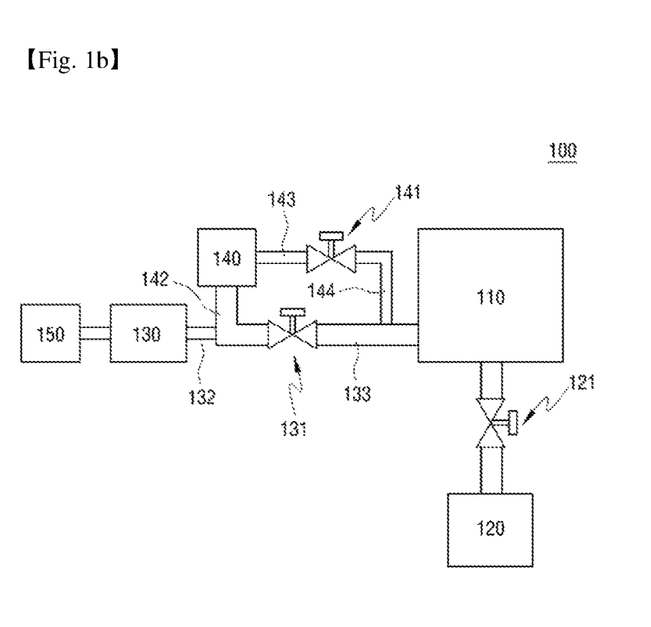
FIG. 1B is a schematic view illustrating the structure of the sterilization apparatus according to the first exemplary embodiment.

FIG. 1A is a schematic perspective view of a sterilization apparatus using a sterilant aqueous solution, according to a first exemplary embodiment of the invention, and FIG. 1B is a schematic view illustrating the structure of the sterilization apparatus according to the first exemplary embodiment.

In the present exemplary embodiment, the term "sterilant" may denote hydrogen peroxide, and the term "sterilant aqueous solution" may denote a hydrogen peroxide solution. In the description that follows, it is assumed that hydrogen peroxide and a hydrogen peroxide solution are used as a sterilant and a sterilant aqueous solution, respectively, for convenience.

The hydrogen peroxide may contain 100 ppm or less of metal ions.

Examples of the metal ions may include ions of a precious metal such as palladium (Pd), platinum (Pt), or the like, ions of a transition metal such as iron (Fe), ions of an alkali metal such as calcium (Ca), magnesium (Mg), potassium (K), sodium (Na), or the like, or phosphorous (P). If the content of the metal ions exceeds 100 ppm, the hydrogen peroxide may be accumulated in a vaporizer, a collector, or a pipe, causing breakdown of valves. A hydrogen peroxide vapor may be easily dissolved upon contact with an accumulation of a precious metal, a transition metal, or an alkali metal, and the metal ions may remain in the vaporizer or the collector, expanding its surface area. As a result, the vaporization efficiency of the hydrogen peroxide may decrease.

Referring to FIGS. 1A and 1B, a sterilization apparatus 100 using hydrogen peroxide includes a sterilization chamber 110.

The sterilization chamber 110 may be a vessel for receiving a target object to be sterilized, such as a medical instrument or a surgical instrument. The sterilization chamber 110 may include a door, which is provided at one side of the sterilization chamber 110 and through which the target enters or exits the sterilization chamber 110.

The sterilization chamber 110 may also include a vacuum pump 120, which is connected to one side of the sterilization chamber 110, and the vacuum pump 120 may form a vacuum state by discharging the gas from the sterilization chamber 110. A vacuum valve 121 capable of controlling an operation of the vacuum pump 120 is connected between the sterilization chamber 110 and the vacuum pump 120.

Referring further to FIGS. 1A and 1B, the sterilization apparatus 100 using a hydrogen peroxide solution, according to the first exemplary embodiment, also includes a vaporizer 130 (also referred to as an evaporator), which is connected to the other side of the sterilization chamber 110 and supplies a hydrogen peroxide vapor to the sterilization chamber 110, and a hydrogen peroxide supply device 150, which supplies hydrogen peroxide to the vaporizer 130.

A vaporization valve 131 may be provided between the sterilization chamber 110 and the vaporizer 130.

The sterilization apparatus 100 using a hydrogen peroxide solution, according to the first exemplary embodiment, also includes a collector 140 (also referred to as a collecting vaporizer), which has one side connected to the vaporizer 130 and the other side connected to the sterilization chamber 110 and concentrates the hydrogen peroxide supplied to the vaporizer 130.

The vaporization valve 131 may be provided between the sterilization chamber 110 and the collector 140.

A collection valve 141 may also be provided between the sterilization chamber 110 and the collector 140.

That is, the vaporization valve 131 and the collection valve 141 may be connected in parallel between the sterilization chamber 110 and the collector 140.

As described above, the vaporization valve 131 may be provided between the sterilization chamber 110 and the vaporizer 130. That is, the vaporization valve 131 may have one side connected to the sterilization chamber 110 and the other side connected in parallel between the vaporizer 130 and the collector 140.

Referring further to FIGS. 1A and 1B, the sterilization apparatus 100 using a hydrogen peroxide solution, according to the first exemplary embodiment, also includes a first connecting pipe 142, which connects the collector 140 and the vaporization valve 131, and a second connecting pipe 133, which connects the vaporization valve 131 and the sterilization chamber 110.

The sterilization apparatus 100 using a hydrogen peroxide solution, according to the first exemplary embodiment, may also include a third connecting pipe 143, which connects the collector 140 and the collection valve 141, and a fourth connecting pipe 144, which connects the collection valve 141 and the sterilization chamber 110.

FIGS. 1A and 1B illustrate the fourth connecting pipe 144 as being connected to the second connecting pipe 133 so as for the vaporization valve 131 and the collection valve 141 to be connected in parallel between the sterilization chamber 110 and the collector 140, but the invention is not limited thereto. That is, alternatively, the fourth connecting pipe 144 may be connected directly to the sterilization chamber 110 so as for the vaporization valve 131 and the collection valve 141 to be connected in parallel between the sterilization chamber 110 and the collector 140.

The sterilization apparatus 100 using hydrogen peroxide may also include a fifth connecting pipe 132, which connects the vaporizer 130 and the vaporization valve 131. FIGS. 1A and 1B illustrate the fifth connecting pipe 132 as being connected to the first connecting pipe 142 so as for the vaporization valve 131 to be connected in parallel to the vaporizer 130 and the collector 140, but the invention is not limited thereto. That is, alternatively, the fifth connecting pipe 132 may be connected directly to the vaporization valve 131 so as for the vaporization valve 131 to be connected in parallel between the vaporizer 130 and the collector 140.

The vaporization valve 131 and the collection valve 141 may control the flow of a fluid in each of the first, second, third, fourth, and fifth connecting pipes 142, 133, 143, 144, and 132 through an "open/close" operation. The "open/close" operation for the vaporization valve 131 and the collection valve 141 may be controlled by an additional controller.

The first connecting pipe 142, which connects the collector 140 and the vaporization valve 131, and the second connecting pipe 133, which connects the vaporization valve 131 and the sterilization chamber 110, may have a larger inner diameter than the other connecting pipes. For example, in response to the third, fourth, and fifth connecting pipes 143, 144, and 132 being ¼-inch pipes, the first and second connecting pipes 142 and 133 may be 1-inch pipes, and this will be described later in detail.

Although not specifically illustrated, temperature control means for controlling the temperature of the sterilization chamber 110, the vaporizer 130, and the collector 140 may be provided. The temperature control means may be a heater, which is obvious to a person skilled in the art to which the invention pertains, and thus, a detailed description of the temperature control means will be omitted.

The collector 140 may include cooling means as temperature control means thereof. The cooling means may use an appraise cooling method such as a direct cooling method using a coolant or a thermoelectric device or an air cooling method using a heat exchanger.

A sterilization method using the sterilization apparatus according to the first exemplary embodiment will hereinafter be described.

Figure 2:
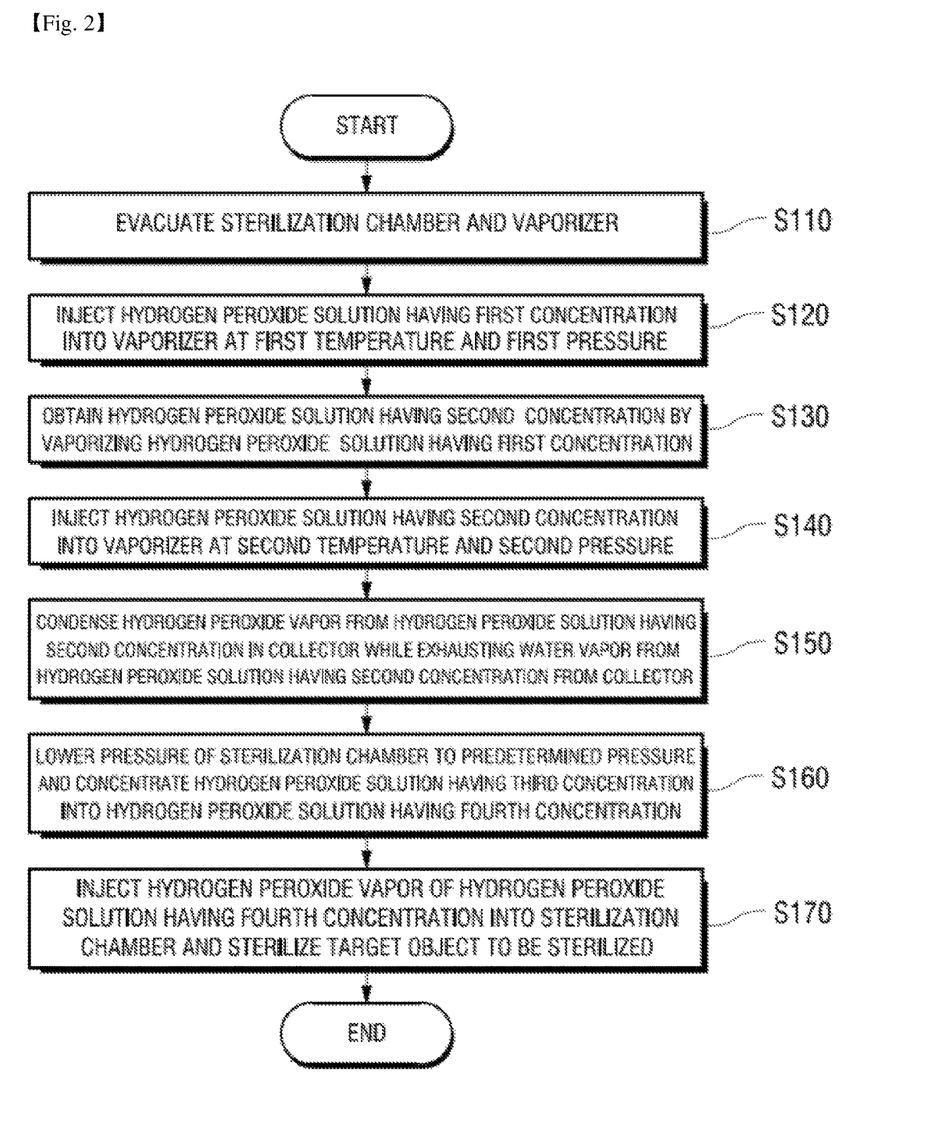
FIG. 2 is a flowchart illustrating a sterilization method of the sterilization apparatus according to the first exemplary embodiment.

FIG. 2 is a flowchart illustrating a sterilization method of the sterilization apparatus according to the first exemplary embodiment.

In the present exemplary embodiment, the term "sterilant" may denote hydrogen peroxide, and the term "sterilant aqueous solution" may denote a hydrogen peroxide solution. In the description that follows, it is assumed that hydrogen peroxide and a hydrogen peroxide solution are used as a sterilant and a sterilant aqueous solution, respectively, for convenience.

The sterilization method according to the present exemplary embodiment will hereinafter be described with reference to FIG. 2 and further reference to FIGS. 1A and 1B.

Referring to FIG. 2, the sterilization method according to the present exemplary embodiment includes evacuating the sterilization chamber 110 (also referred to as a pasteurization chamber) and the vaporizer 130 to a vacuum (S110).

The sterilization chamber 110 and the vaporizer 130 may be evacuated by turning on the vacuum pump 120 and opening the vacuum valve 121.

S110, i.e., a step of evacuating the sterilization chamber and the vaporizer, may be continued until S160, which will be described later, begins, and may be completed in response to the sterilization chamber 110 reaching a predetermined pressure and a hydrogen peroxide liquid with moisture removed therefrom being collected in the collector.

To evacuate the vaporizer 130, the vaporization valve 131 between the sterilization chamber 110 and the vaporizer 130 or the collection valve 141 between the sterilization chamber 110 and the collector 140 may be opened to be in communication with the sterilization chamber currently being evacuated and thus to lower the pressure below atmospheric pressure, and may be closed in a subsequent step.

During the evacuation of the sterilization chamber 110 and the vaporizer 130, the sterilization chamber and the vaporizer may be maintained at a predetermined temperature by the aforementioned temperature control means.

Thereafter, the sterilization method according to the present exemplary embodiment includes introducing a hydrogen peroxide solution having a first concentration into the vaporizer 130 at a first temperature and a first pressure (S120).

The introduction of the hydrogen peroxide solution may be performed by the hydrogen peroxide supply device 150, which stores the hydrogen peroxide solution. Although not specifically illustrated in FIGS. 1A and 1B, a hydrogen peroxide supply control valve (not illustrated) may be provided between the vaporizer 130 and the hydrogen peroxide supply device 150, and thus, an appropriate amount of the hydrogen peroxide solution may be supplied.

The first concentration may be 60 wt % or less.

In reality, the concentration of a hydrogen peroxide solution that can be handled is generally limited to 60 wt % or lower, and thus, it is difficult to use a hydrogen peroxide solution with a concentration of higher than 60 wt % as a sterilant.

That is, the first concentration is the concentration of a hydrogen peroxide solution that can be handled, and is not necessarily of great significance in understanding the subject matter of the invention.

The first temperature may range from 60° C. to 70° C., and the first pressure may be 800 mb or atmospheric pressure.

In S120, while the hydrogen peroxide solution having the first concentration is being introduced into the vaporizer 130, the vaporization valve 131 and the collection valve 141 may be closed, or may remain open depending on the type of the hydrogen peroxide supply device.

In S120, the sterilization chamber 110 may have a pressure of 800 mb to atmospheric pressure and a temperature of 38° C. to 42° C.

The first temperature may be higher than the temperature of the sterilization chamber.

The first temperature may correspond to the temperature of the vaporizer at which more water vapor can be vaporized from the hydrogen peroxide solution. During the vaporization of water vapor, a very strong endothermic reaction occurs, strongly suppressing the speed of vaporization.

To enhance the speed of vaporization, the pressure of the vaporizer may be lowered so as to increase the degree of vacuum, in which case, the vaporization rate of hydrogen peroxide may also increase, resulting in an increase in the consumption of hydrogen peroxide. Also, sufficient energy for vaporizing the hydrogen peroxide solution may not be properly provided at low temperature. Thus, the first temperature may be set to be higher than at least the temperature of the sterilization chamber.

Thereafter, the sterilization method according to the present exemplary embodiment includes obtaining a hydrogen peroxide solution having a second solution by vaporizing the hydrogen peroxide solution having the first concentration (S130).

That is, in response to the hydrogen peroxide solution having the first concentration being vaporized in the vaporizer 130 (i.e., water being removed from the hydrogen peroxide solution), the hydrogen peroxide solution having the second concentration is obtained.

The second concentration may be 75 wt % to 85 wt %. Accordingly, S130 may be a primary hydrogen peroxide solution concentration step for obtaining a hydrogen peroxide solution having a concentration of 75 wt % to 85 wt % by vaporizing a hydrogen peroxide solution having a concentration of 60 wt % or less.

In general, water evaporates more quickly than hydrogen peroxide at a given temperature and pressure because the vapor pressure of water is higher than the vapor pressure of hydrogen peroxide. Also, since the molecular weight of water is lower than the molecular weight of hydrogen peroxide, water diffuses more quickly than hydrogen peroxide.

Since water (or moisture) evaporates and diffuses more quickly than hydrogen peroxide at a given temperature and pressure, the water in a hydrogen peroxide solution also evaporates and diffuses into the air more quickly than the hydrogen peroxide in the hydrogen peroxide solution. Thus, the hydrogen peroxide solution having the second concentration may be obtained.

In S130, evaporated water may be exhausted by the vacuum pump via the sterilization chamber 110. Thus, in S130, the vacuum pump 120 may be turned on, and the vacuum valve 121 and the vaporization valve 131 may be opened, thereby performing evacuation.

In S130, due to an endothermic reaction during the vaporization of the hydrogen peroxide solution having the first concentration, the temperature of the vaporizer 130 may temporarily decrease and may thus be in the range of 55° C. to 65° C., and the vaporizer 130 may have a pressure of 30 mb to 800 mb.

While evaporated water is being exhausted through the sterilization chamber 110 and the vacuum pump, the sterilization chamber 110 may have a pressure of 10 mb to 600 mb and a temperature of 45° C. to 55° C., and the collector 140 may have a pressure of 20 mb to 500 mb and a temperature of 35° C. to 45° C.

Thereafter, the sterilization method according to the present exemplary embodiment includes injecting the hydrogen peroxide solution having the second concentration into the collector at a second temperature and a second pressure (S140).

To inject the hydrogen peroxide solution having the second concentration into the collector 140 at the second temperature and the second pressure, the vacuum pump 120 may be turned on, the vacuum valve 121 may be opened, the vaporization valve 131 may be closed, and the collection valve 141 may be turned on.

The second temperature may be 35° C. to 42° C., and the second pressure may be 8 mb to 50 mb.

While the hydrogen peroxide solution having the second concentration is being transferred from the vaporizer 130 to the collector 140, the vaporizer 130 may have a pressure of 10 mb to 60 mb and a temperature of 55° C. to 60° C. The hydrogen peroxide solution having the second concentration may be transferred from the vaporizer 130 to the collector 140 via the second connecting pipe 132 and the first connecting pipe 142.

Even in S140, the evacuation of the sterilization chamber 110 is continued so that the sterilization chamber 110 may have a pressure of 1 mb to 10 mb and a temperature of 45° C. to 55° C.

The second temperature may be lower than the temperature of the sterilization chamber.

The second temperature may correspond to the temperature of the collector during the collection of the hydrogen peroxide solution having the second concentration. In response to the temperature of a hydrogen peroxide vapor saturated from the vaporizer being higher than the temperature of the sterilization chamber, the hydrogen peroxide vapor may be released through the sterilization chamber, instead of being condensed in the collector.

Even if some of the hydrogen peroxide vapor is condensed at early stages of S140 and S150, the condensed hydrogen peroxide may easily evaporate again and thus may not remain in the collector as long as the temperature of the collector is higher than the temperature of the sterilization chamber, because the vaporization heat of hydrogen peroxide is lower than the vaporization heat of water vapor. As a result, S170 may not be able to be performed. Thus, the second temperature may be lower than at least the temperature of the sterilization chamber.

As mentioned above, S130, i.e., the step of obtaining the hydrogen peroxide solution having the second concentration by vaporizing the hydrogen peroxide solution having the first concentration, may be performed, and then S140, i.e., a step of injecting the hydrogen peroxide solution having the second concentration into the collector at the second temperature and the second pressure, may be performed.

Instead, a method in which S140 is performed without performing S130, i.e., the hydrogen peroxide solution having the first concentration is directly injected into the collector, may be taken into consideration. This method may be inappropriate for the reasons that will be explained below.

Table 1 shows the vaporization rate of hydrogen peroxide vapor in various hydrogen peroxide solutions having different solutions.

TABLE 1

| Temperature | HP wt % | | | | | | | | | | |
| --- | --- | --- | --- | --- | --- | --- | --- | --- | --- | --- | --- |
| | 50% | 55% | 60% | 65% | 70% | 75% | 80% | 83% | 85% | 90% | 95% |
| 50° C. | 8% | 10% | 13% | 17% | 23% | 31% | 40% | 47% | 52% | 66% | 82% |
| 60° C. | 9% | 11% | 14% | 19% | 25% | 32% | 42% | 48% | 53% | 67% | 83% |
| 70° C. | 9% | 12% | 15% | 20% | 26% | 34% | 43% | 50% | 55% | 68% | 84% |

Referring to Table 1, the higher the concentration of a hydrogen peroxide solution and the higher the temperature, the higher the vaporization rate of hydrogen peroxide vapor relative to the vaporization rate of water vapor.

For example, at a temperature of 50° C., the vaporization rate of hydrogen peroxide vapor is 13% in a hydrogen peroxide solution having a concentration of 60 wt %, which means that the rest of the hydrogen peroxide solution, i.e., 87% of the hydrogen peroxide solution, is water vapor, and the vaporization rate of hydrogen peroxide vapor is 40% in a hydrogen peroxide solution having a concentration of 80 wt %, which means that the rest of the hydrogen peroxide solution, i.e., 60% of the hydrogen peroxide solution, is water vapor.

That is, performing S140 without performing S130 may mean injecting a hydrogen peroxide solution having a concentration of for example, 60 wt %, into the collector, and performing S130 and then S140 may mean injecting a hydrogen peroxide solution having a concentration of 80 wt % into the collector.

In the case of performing S140 without performing S130, the ratio of water vapor passing through the collector at an early stage of S140 may be relatively high, compared to the case of performing S130 and then S140.

If a hydrogen peroxide solution with a high ratio of water vapor to hydrogen peroxide vapor is injected into the collector, the water vapor may be condensed in the collector because of a high pressure in the collector (for example, a pressure higher than a saturated water vapor pressure of 75 mb when the temperature of the collector is 40° C.).

If the water vapor is condensed in the collector, there is a limit in the degree to which a hydrogen peroxide solution can be concentrated due to the condensed water vapor.

In the present exemplary embodiment, to prevent water vapor from being condensed first in the collector to limit the degree to which a hydrogen peroxide solution can be concentrated, S130, i.e., the step of obtaining the hydrogen peroxide solution having the second concentration by vaporizing the hydrogen peroxide solution having the first concentration, may be performed first, and then S140, i.e., the step of injecting the hydrogen peroxide solution having the second concentration into the collector at the second temperature and the second pressure, may be performed.

Thereafter, the sterilization method according to the present exemplary embodiment includes condensing hydrogen peroxide vapor from the hydrogen peroxide solution having the second concentration in the collector, and exhausting water vapor from the hydrogen peroxide solution having the second concentration from the collector (S150). As already mentioned above, water evaporates more quickly than hydrogen peroxide at a given temperature and pressure because the vapor pressure of water is higher than the vapor pressure of hydrogen peroxide. Also, since the molecular weight of water is lower than the molecular weight of hydrogen peroxide, water diffuses into the air more quickly than hydrogen peroxide. Since water (or moisture) evaporates and diffuses more quickly than hydrogen peroxide at a given temperature and pressure, the water in a hydrogen peroxide solution also evaporates and diffuses into the air more quickly than the hydrogen peroxide in the hydrogen peroxide solution. Thus, hydrogen peroxide vapor is condensed in the collector, and water vapor is exhausted from the collector. As a result, a hydrogen peroxide solution having a third concentration may be obtained.

That is, water has a higher vapor pressure than hydrogen peroxide, and thus, hydrogen peroxide vapor is condensed more easily than water vapor. Accordingly, a hydrogen peroxide solution condensed in the collector may contain a higher concentration of hydrogen peroxide than the hydrogen peroxide solution having the second concentration.

In S140, hydrogen peroxide vapor and water vapor may sequentially pass through the fifth connecting pipe, the first connecting pipe, the third connecting pipe, and the fourth connecting pipe, and the temperature of one or more small-inner diameter connecting pipes among the first, third, fourth, and fifth connecting pipes needs to be higher than the temperature of the collector 140.

More specifically, if the temperature of a connecting pipe to or from the collector is lower than the temperature of the collector, hydrogen peroxide vapor may remain condensed in the connecting pipe. Hydrogen peroxide vapor condensed in a connecting pipe with a small inner diameter may be exposed to a high temperature in S170, and thus, the content of water vapor may undesirably increase due to the decomposition of hydrogen peroxide at the stage of entering the sterilization chamber.

As shown in Table 1, once the concentration of a hydrogen peroxide solution is as high as, for example, less than 85 wt %, the ratios of water and hydrogen peroxide in the hydrogen peroxide solution are similar to each other, and the concentration of the hydrogen peroxide solution by a water/hydrogen peroxide vaporization ratio lowers the efficiency of concentration of the hydrogen peroxide solution.

At a given pressure, the temperature at which hydrogen peroxide vapor is condensed differs from the temperature at which water vapor is condensed. For example, at a temperature of 35° C., hydrogen peroxide is condensed at a pressure of 5 mb or higher, and water vapor is condensed at a pressure of 55 mb or higher.

Accordingly, when the temperature of the collector is 35° C. during the evacuation of the collector via the collection valve, hydrogen peroxide vapor may be condensed, and water vapor may be exhausted from the collector if the pressure of the collector is in the range of 5 mb to 55 mb.

The third concentration may be 90 wt % to 95 wt %. Accordingly, S150 may be a secondary hydrogen peroxide solution concentration step for obtaining a hydrogen peroxide solution having a concentration of 90 wt % to 95 wt % by vaporizing a hydrogen peroxide solution having a concentration of 75 wt % to 85 wt %.

In the present exemplary embodiment, S140, i.e., the step of injecting the hydrogen peroxide solution having the second concentration into the collector at the second temperature and the second pressure, and S150, i.e., a step of condensing hydrogen peroxide vapor from the hydrogen peroxide solution having the second concentration while exhausting water vapor from the hydrogen peroxide solution having the second concentration from the collector, may be sequentially performed, but the invention is not limited thereto. That is, alternatively, S140 and S150 may be performed at the same time.

In other words, the hydrogen peroxide solution having the second concentration may be injected into the collector at the second temperature and the second pressure, and at the same time, hydrogen peroxide vapor from the hydrogen peroxide solution having the second concentration may be condensed while exhausting water vapor from the hydrogen peroxide solution having the second concentration from the collector.

In S150, evaporated water may be exhausted via the vacuum pump. Thus, in S150, the vacuum pump 120 may be turned on, and the vaporization valve 131 may be opened so as to exhaust evaporated water. Also, to exhaust evaporated water through the vacuum pump, the collection valve 141 may be opened.

Thereafter, the sterilization method according to the present exemplary embodiment includes lowering the pressure of the sterilization chamber to a predetermined pressure and obtaining a hydrogen peroxide solution having a fourth concentration by concentrating the hydrogen peroxide solution having the third concentration (S160).

The predetermined pressure may be a pressure for sterilizing a target object in the sterilization chamber. In response to the sterilant being hydrogen peroxide vapor, a vacuum state for facilitating the diffusion of hydrogen peroxide vapor needs to be established.

Thus, the predetermined pressure may be 0.5 mb to 1.3 mb, and the temperature of the sterilization chamber 110 may be 45° C. to 55° C.

The fourth concentration may be 95 wt % or higher. Accordingly, S160 may be a tertiary hydrogen peroxide solution concentration step for obtaining a hydrogen peroxide solution having a concentration of 95 wt % or higher by vaporizing a hydrogen peroxide solution having a concentration of 90 wt % to 95 wt %.

In S160, evaporated water may be exhausted via the vacuum pump. Thus, in S160, the vacuum pump 120 may be turned on, and the vacuum valve 121 may be opened so as to exhaust evaporated water.

In S160, the collection valve 141 may be repeatedly opened and closed.

As the hydrogen peroxide solution having the third concentration is concentrated into the hydrogen peroxide solution having the fourth concentration, i.e., as the concentration of a hydrogen peroxide solution increases, the pressure at which hydrogen peroxide can be vaporized decreases.

At a given temperature of for example, 45° C., hydrogen peroxide in a hydrogen peroxide solution having a concentration of 80 wt % is vaporized at a pressure of about 20 mb or lower, but hydrogen peroxide in a hydrogen peroxide solution having a concentration of 90 wt % is vaporized only at a pressure of about 11 mb or lower.

During the concentration of the hydrogen peroxide solution having the third concentration into the hydrogen peroxide solution having the fourth concentration, not only water, but also hydrogen peroxide, evaporates, thereby making it difficult to concentrate a hydrogen peroxide solution to more than a particular level.

That is, the decomposition of a high concentration of hydrogen peroxide may be continued, and moisture generated during the decomposition of the hydrogen peroxide may lower the concentration of the hydrogen peroxide.

To remove a small amount of such impurities as moisture, the pressure may be repeatedly increased and lowered within the range of 0.1 mb to 2 mb, in which case, moisture may be effectively removed while suppressing the vaporization of hydrogen peroxide.

This type of moisture removal may take time when the concentration of a hydrogen peroxide solution is low, but may be effective for the removal of a small amount of moisture from a hydrogen peroxide solution having a high concentration and at least for the maintenance of the high concentration of the hydrogen peroxide solution.

Due to the lowering of the pressure of the sterilization chamber to the predetermined pressure, the pressure of the collector 140 containing the hydrogen peroxide solution having the third concentration may continue to decrease, and as a result, hydrogen peroxide may be easily vaporized at a low pressure. To address this problem, the collection valve 141 may be repeatedly opened and closed, thereby preventing the pressure of the collector 140 from continuously decreasing.

In S160, the collector 140 may have a pressure of 5 mb to 10 mb and a temperature of 35° C. to 40° C., and the vaporizer 130 may have a pressure of 7 mb to 10 mb and a temperature of 60° C. to 70° C.

In S160, the hydrogen peroxide solution in the vaporizer is completely consumed, and thus, the temperature of the vaporizer is recovered in a vacuum state. A high concentration of hydrogen peroxide is collected in the collector while a small amount of moisture is being removed therefrom, or stays in the collector while being maintained at a predetermined pressure.

In S160, the temperature of the collector may be further lowered by the temperature control means to prevent an excessive consumption of hydrogen peroxide.

Thereafter, the sterilization method according to the present exemplary embodiment includes injecting hydrogen peroxide vapor of the hydrogen peroxide solution having the fourth concentration into the sterilization chamber and sterilizing the target object in the sterilization chamber (S170).

In S170, to inject the hydrogen peroxide vapor of the hydrogen peroxide solution having the fourth concentration from the collector 140 into the sterilization chamber 110, the vaporization valve 131 may be opened, and the collection valve may be opened or closed.

That is, hydrogen peroxide may be transferred from the collector 140 to the sterilization chamber 110 via the first and second connecting pipes 142 and 133.

As already mentioned above, the first connecting pipe 142, which connects the collector 140 and the vaporization valve 131, and the second connecting pipe 133, which connects the vaporization valve 131 and the sterilization chamber 110, may have a larger inner diameter than the other connecting pipes, i.e., the third, fourth, and fifth connecting pipes 143, 144, and 132. For example, in response to the third, fourth, and fifth connecting pipes 143, 144, and 132 being ¼-inch pipes, the first and second connecting pipes 142 and 133 may be 1-inch pipes.

This is for preventing hydrogen peroxide vapor from infiltrating into the fifth connecting pipe 132 while being transferred into the sterilization chamber 110 via the first and second connecting pipes 142 and 133, and hydrogen peroxide vapor may not be introduced into the first connecting pipe 142, which has a relatively large inner diameter, but not into the fifth connecting pipe 132, which has a relatively small inner diameter.

In the present exemplary embodiment, hydrogen peroxide vapor not having a high temperature may be injected into the sterilization chamber to sterilize the target object.

If hydrogen peroxide vapor, which is vaporized in the collector when yet to be sufficiently saturated, enters the sterilization chamber while having a higher temperature than the sterilization chamber, the density of the hydrogen peroxide vapor may become excessively high in the path to the sterilization chamber, and thus, the hydrogen peroxide vapor may be easily condensed. As a result, the absolute amount of hydrogen peroxide that can be diffused into the sterilization chamber in a gaseous state may decrease, and a diffusion effect for sterilization may be adversely affected.

In the present exemplary embodiment, pipes in the path between the collector 140 and the sterilization chamber 110 may have a larger inner diameter than other pipes. The larger the inner diameter of a pipe, the larger the amount of gas that can be transferred via the pipe. Thus, a pipe having a large inner diameter may considerably increase the vaporization driving force resulting from the degree of vacuum by as much as the amount of gas that can be transferred via the pipe, and may thus prevent the temperature of hydrogen peroxide vapor from increasing.

That is, the less the amount of hydrogen peroxide vapor, the longer the amount of time that the hydrogen peroxide vapor is stayed in the collector and the higher the speed of decomposition of the hydrogen peroxide vapor in the collector that requires an increase in the temperature for the vaporization and the transportation of hydrogen peroxide. Thus, the concentrations of water vapor and an oxygen gas, which are the by-products of the decomposition of the hydrogen peroxide solution, increase. This, however, contradicts the purpose of minimizing the amount of water vapor, which interferes with the diffusion of hydrogen peroxide, as performed in the previous step, and may weaken the sterilization performance.

Thus, in the present exemplary embodiment, pipes having a large inner diameter may be provided in the path between the collector 140 and the sterilization chamber 110, and hydrogen peroxide vapor may be injected into the sterilization chamber when not having a high temperature. Accordingly, the decomposition of hydrogen peroxide by temperature may be minimized, hydrogen peroxide may be sufficiently diffused in a gaseous state, and the access of hydrogen peroxide vapor to the target object may be facilitated. As a result, an excellent sterilization effect may be achieved.

In response to the hydrogen peroxide solution having the fourth concentration being injected into the sterilization chamber 110, hydrogen peroxide may be diffused into the sterilization chamber in a gaseous state, and the heating rate of the collector 140 may be controlled such that the vaporization of the hydrogen peroxide may be almost complete before the temperature of the collector 140 reaches the temperature of the sterilization chamber.

That is, to promote the vaporization of hydrogen peroxide, the collector 140 may be heated by the temperature control means, and the rate of the heating of the collector may be controlled such that the vaporization of the hydrogen peroxide is at least 80% complete before the temperature of the collector reaches the temperature of the sterilization chamber.

In S170, the sterilization chamber 110 may have a pressure of 0.5 mb to 15 mb and a temperature of 45° C. to 55° C.

Also, the collector 140 have a pressure of 0.5 mb to 15 mb and a temperature of 30° C. to 70° C., and the vaporizer 130 may have a pressure of 0.5 mb to 15 mb and a temperature of 60° C. to 70° C. or higher.

The pressure and temperature conditions in each of the steps of the sterilization method according to the present exemplary embodiment are as shown in Table 2 below.

The states of the vacuum pump and the valves in each of the steps of the sterilization method according to the present exemplary embodiment are as shown in Table 3 below.

TABLE 3

| Classification | Vacuum Pump | Vacuum Valve | Vaporization Valve | Collection Valve |
| --- | --- | --- | --- | --- |
| S120 | On or off | Open or Close | Close | Close |
| S130 | On | Open | Open | Open or close |
| S140, S150 | On | Open | Close | Open |
| S160 | On | Open | Close | Repeatedly open and close |
| S170 | Off | Close | Open | Open or close |

As described above, a highly-concentrated hydrogen peroxide solution may preferably be used to improve the sterilization performance. In reality, the concentration of a hydrogen peroxide solution that can be handled is generally limited to 60 wt % or lower, and thus, it is difficult to use a hydrogen peroxide solution with a concentration of higher than 60 wt % as a sterilant.

On the other hand, in the present exemplary embodiment, a hydrogen peroxide solution having a concentration of 95 wt % or higher may be obtained through multiple concentration steps and may be used as a sterilant. Also, water vapor's interference with diffusion may be reduced, and as a result, a sterilization effect may be considerably improved.

Also, by performing S140 and S150 after S130, i.e., the step of obtaining the hydrogen peroxide solution having the second concentration by removing moisture from the hydrogen peroxide solution having the first concentration, the probability of moisture being in contact with the collector may be reduced.

Also, by lowering the saturated vapor pressure of moisture according to the pressure and temperature of the collector, i.e., the "vaporization/condensation boundary pressure" of a hydrogen peroxide solution when injecting the hydrogen peroxide solution into the collector, a condition may be established in which moisture can be prevented from condensing even in contact with the collector.

Experimental examples of the invention will hereinafter be described, but the invention is not limited thereto. The following experimental examples are for verifying the effects of the presence or absence of S130 and the effects of combinations of connecting pipes of various inner diameters for connecting the vaporizer, the collector, and the sterilization chamber.

TABLE 2

| | Vaporizer | | Collector | | Sterilization chamber | |
| --- | --- | --- | --- | --- | --- | --- |
| Classification | Pressure (mb) | Temperature (° C.) | Pressure (mb) | Temperature (° C.) | Pressure (mb) | Temperature (° C.) |
| S120 | 800~Atmospheric Pressure | 60~70 | 800~Atmospheric Pressure | 38~42 | 600~Atmospheric Pressure | 45~55 |
| S130 | 30~800 | 55~65 | 20~500 | 35~40 | 10~600 | 45~55 |
| S140, S150 | 10~60 | 55~60 | 8~50 | 35~42 | 1~10 | 45~55 |
| S160 | 7~10 | 60~70 | 5~10 | 35~40 | 0.5~1.3 | 45~55 |
| S170 | 0.5~15 | 60~70 | 0.5~15 | 30~70 | 0.5~15 | 45~55 |

Experimental Examples

In Experimental Examples 1 to 9, a sterilization chamber with a capacity of 130 L was used, and the temperature of the sterilization chamber was set to 50° C. As mentioned above with reference to FIG. 1B, the combined length of the first and second connecting pipes was set to 250 mm, the combined length of the third and fourth connecting pipes was set to 800 mm, and the length of the fifth connecting pipe was set to 200 mm.

6 ml of a hydrogen peroxide solution having a concentration of 59 wt % was provided as a hydrogen peroxide solution having a first concentration.

The amount of injection of the hydrogen peroxide solution and the length of the connecting pipes may be arbitrarily determined, and may be modified in consideration of the volume of the sterilization chamber, the size of the connecting tubes, and the exhaust capacity of a vacuum pump.

For example, if a vacuum pump having an exhaust capacity of 600 L/min is used with a sterilization chamber having a volume of 130 L, the first and second connecting pipes may have a length of 250 mm or less, and may have an inner diameter of about ½ inches or larger, the third and fourth connecting pipes may have a length of 600 mm to 1000 mm and an inner diameter of ⅜ inches or less, the fifth connecting pipe may have a length of 200 mm and an inner diameter of ⅜ inches or less, and 6 ml of a hydrogen peroxide solution having a concentration of 59 wt % may be injected.

Alternatively, if a vacuum pump having an exhaust capacity of 200 L/min is used with a sterilization chamber having a volume of 50 L, the first and second connecting pipes may have a length of 150 mm or less, and may have an inner diameter of about ⅜ inches or larger, the third and fourth connecting pipes may have a length of 400 mm to 1000 mm and an inner diameter of ¼ inches or less, the fifth connecting pipe may have a length of 100 mm to 300 mm and an inner diameter of ¼ inches or less, and 2.5 ml of a hydrogen peroxide solution having a concentration of 59 wt % may be injected.

Table 4 below shows experimental conditions according to each of Experimental Examples 1 to 9, and particularly, the conditions regarding the temperature and pressure of the vaporizer in S130, the temperature and pressure of the collector in S140 and S150, and the sizes of the connecting pipes when using a sterilization chamber having a capacity of 130 L. In Table 4, the pressure of the vaporizer in S130 is the final pressure of the vaporizer at the time of completion of S130 in response to the vaporization valve being closed, the pressure of the collector in S140 and S150 is the initial pressure at the time of the beginning of S140 and S150 in response to the vaporization valve being closed.

TABLE 4

| Experimental Example No. | S130 (Vaporizer) | | S140/S150 (Collector) | | First and Second Connecting Pipes | Third and Fourth Connecting Pipes | Fifth Connecting Pipe |
|---|---|---|---|---|---|---|---|
| | Temperature | Pressure (Min.) | Second Temperature | Second Pressure (Max.) | | | |
| 1 | 67° C. | — | 40° C. | Atmospheric Pressure | 1 inch | ¼ inches | ¼ inches |
| 2 | 67° C. | 100 mb | 40° C. | 80 mb | 1 inch | ¼ inches | ¼ inches |
| 3 | 67° C. | 100 mb | 35° C. | 80 mb | 1 inch | ¼ inches | ¼ inches |
| 4 | 60° C. | 60 mb | 35° C. | 48 mb | 1 inch | ¼ inches | ¼ inches |
| 5 | 63° C. | 40 mb | 40° C. | 32 mb | 1 inch | ¼ inches | ¼ inches |
| 6 | 63° C. | 40 mb | 40° C. | 32 mb | ½ inches | ¼ inches | ¼ inches |
| 7 | 63° C. | 40 mb | 40° C. | 32 mb | ½ inches | ⅜ inches | ⅜ inches |
| 8 | 63° C. | 40 mb | 40° C. | 32 mb | ½ inches | ½ inches | ½ inches |
| 9 | 63° C. | 40 mb | 40° C. | 32 mb | ¼ inches | ¼ inches | ¼ inches |

Referring to Table 4, in Experimental Examples 4 to 9, S130, i.e., the step of obtaining a hydrogen peroxide solution having the second concentration by vaporizing a hydrogen peroxide solution having the first concentration, and then S140, i.e., the step of injecting the hydrogen peroxide solution having the second concentration into the collector at the second temperature and the second pressure, were performed, in Experimental Example 1, S140 was performed without performing S130, i.e., the hydrogen peroxide solution having the first concentration was vaporized and directly injected into the collector, and in Experimental Examples 2 and 3, S130 was performed, but only insufficiently.

Table 5 below shows the fourth concentration in S160, which varies depending on whether S130 was performed.

TABLE 5

| Experimental Example No. | S160 Fourth Concentration (wt %) |
|---|---|
| 1 | 90 |
| 2 | 92 |
| 3 | 90 |
| 4 | 96 |
| 5 | 97 |
| 6 | 97 |
| 7 | 98 |
| 8 | 99 |
| 9 | 96 |

Referring to Table 4, in the case of Experimental Example 1 in which S140 was performed without performing S130 and Experimental Examples 2 and 3 in which S130 was insufficiently performed and then S140 was performed, not only hydrogen peroxide vapor, but also water vapor, is highly likely to make a contact with, and condense in, the collector at a pressure higher than the saturated vapor pressure of water (i.e., 75 mb and 56 mb at a given temperature of the collector (i.e., 40° C. and 35° C.), and any moisture that remains as impurities increases the saturated vapor pressure of a hydrogen peroxide solution condensed in the collector and thus makes it difficult to further concentrate the hydrogen peroxide solution.

To identify the relationship between concentration efficiency and a sterilization effect, an experiment was conducted as follows.

To identify a sterilization effect, *Bacillus Stearothermophilus* viable spores, which are commonly known as a hydrogen peroxide sterilization indicator, were used as a biological indicator.

A stainless steel disc inoculated with $1.6 \times 10^6$ *Bacillus Stearothermophilus* viable spores was inserted into the PCD center of a stainless steel tube (with a length of 500 mm) simulating a rigid endoscope as an object to be sterilized, 10 PCDs were prepared for each inner diameter (Φ0.5, Φ0.7, and Φ1.0), and each of the PCDs was individually packaged in a Tyvek-Mylar pouch and was added during each period of the experiment.

Thereafter, in response to the sterilization period being complete, the viable spore disc was taken out of the PCD center of the stainless steel tube, inserted into a soybean casein digest medium, cultivated at a temperature of 55° C. for seven days, and observed for the growth of any surviving microorganisms. The absence of any microbial growth means a negative with no microorganisms capable of reproduction, i.e., a successful sterilization, and the presence of microbial growth means a positive, i.e., sterilization failure.

make a contact with, and condense in, the collector, and as a result, any moisture that remains as impurities increases the saturated vapor pressure of a hydrogen peroxide solution condensed in the collector and thus makes it difficult to further concentrate the hydrogen peroxide solution.

After comparing Experimental Examples 4 through 7 with Experimental Examples 8 and 9, it is apparent that excellent sterilization results can be obtained when the first connecting pipe 142 connecting the collector 140 and the vaporization valve 131 and the second connecting pipe 133 connecting the vaporization valve 131 and the sterilization chamber 110 have a larger inner diameter than the other connecting pipes.

When the first connecting pipe 142 connecting the collector 140 and the vaporization valve 131 and the second connecting pipe 133 connecting the vaporization valve 131 and the sterilization chamber 110 have a smaller inner diameter than the other connecting pipes, the amount of gas transferred from the collector to the sterilization chamber decreases, the speed of decomposition of hydrogen peroxide vapor in the collector that requires an increase in the

TABLE 6

| Experimental Example No. | S160 Fourth Concentration (wt %) | Chamber Pressure (mb) in S170 (Collector Temperature = Chamber Temperature = 50° C.) | | | Sterilization Results n/N (n = Number of Negatives, N = Total Number) | | |
|---|---|---|---|---|---|---|---|
| | | Initial | Rate of Increase | Final | Φ0.5, L500 | Φ0.7, L500 | Φ1.0, L500 |
| 1 | 90 | 15.1 | 61% | 24.8 | 1/10 | 2/10 | 7/10 |
| 2 | 92 | 15.2 | 83% | 18.3 | 1/10 | 4/10 | 10/10 |
| 3 | 90 | 15.1 | 79% | 19.2 | 0/10 | 6/10 | 10/10 |
| 4 | 96 | 13.8 | 81% | 17 | 9/10 | 10/10 | 10/10 |
| 5 | 97 | 12.8 | 88% | 14.5 | 10/10 | 10/10 | 10/10 |
| 6 | 97 | 12.6 | 88% | 14.4 | 10/10 | 10/10 | 10/10 |
| 7 | 98 | 9 | 89% | 10.1 | 9/10 | 10/10 | 10/10 |
| 8 | 99 | 5 | 83% | 6 | 3/10 | 7/10 | 9/10 |
| 9 | 96 | 8 | 47% | 17 | 2/10 | 6/10 | 10/10 |

Referring to Table 5, Experimental Examples 5 and 6, which represent the benefits of exemplary embodiments of the invention the most, exhibit a sufficiently high fourth concentration, a sufficient collection amount and an excellent sterilization effect, and the same results can be obtained when the inner diameter of the first and second connecting pipes are ½ inches or larger.

Experimental Examples 4 and 7 show one positive sterilization result for "Φ0.5" and "L500", which, however, may be regarded as an experimental error, and also exhibit a sufficiently high fourth concentration, a sufficient collection amount and an excellent sterilization effect.

On the other hand, Experimental Examples 1 through 3 provide a fourth concentration of only 95 wt % or lower and poor sterilization results.

Experimental Examples 8 and 9 provide a fourth concentration of 95 wt % or higher, but poor sterilization results.

That is, after comparing Experimental Examples 1 through 3 with Experimental Examples 4 through 7, it may be understood that Experimental Example 1 in which S140 was performed without performing S130 and Experimental Examples 2 and 3 in which S130 was insufficiently performed and then S140 was performed provide a fourth concentration of 95 wt % or lower because not only hydrogen peroxide vapor, but also water vapor, is highly likely to temperature for the vaporization and transfer of hydrogen peroxide increases, and the concentrations of water vapor and an oxygen gas, which are the by-products of the decomposition of a hydrogen peroxide solution, increase. This, however, contradicts the purpose of minimizing the amount of water vapor, which interferes with the diffusion of hydrogen peroxide, as performed in the previous step, and may weaken the sterilization performance.

Figure 3:
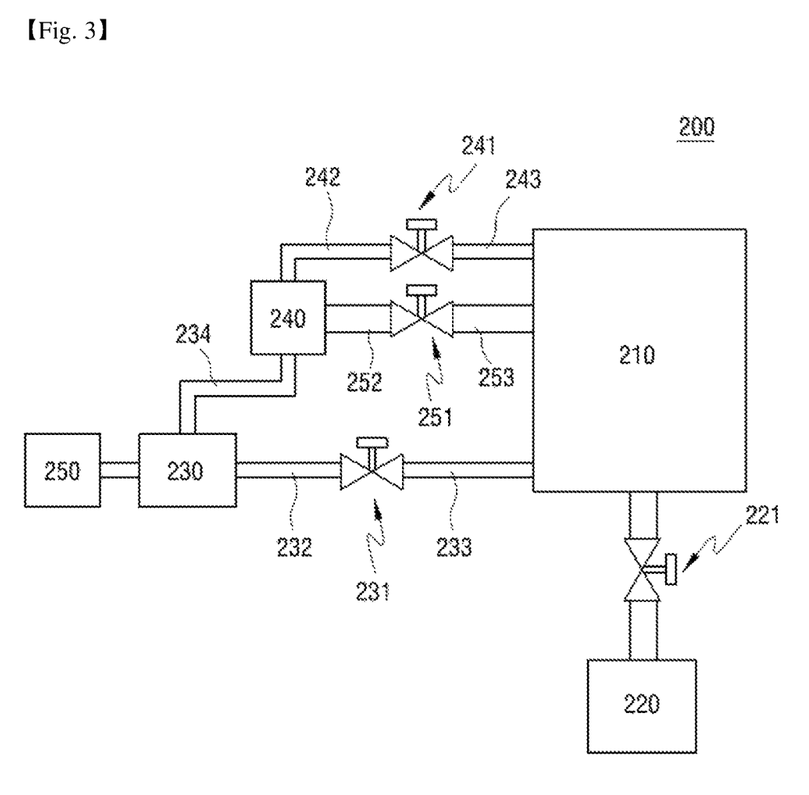
FIG. 3 is a schematic view illustrating the structure of a sterilization apparatus using a sterilant aqueous solution, according to a second exemplary embodiment of the invention.

FIG. 3 is a schematic view illustrating the structure of a sterilization apparatus using a sterilant aqueous solution, according to a second exemplary embodiment of the invention.

In the present exemplary embodiment, the term "sterilant" may denote hydrogen peroxide, and the term "sterilant aqueous solution" may denote a hydrogen peroxide solution. In the description that follows, it is assumed that hydrogen peroxide and a hydrogen peroxide solution are used as a sterilant and a sterilant aqueous solution, respectively, for convenience.

The sterilization apparatus according to the second exemplary embodiment may be the same as the sterilization apparatus according to the first exemplary embodiment except for a few aspects that will hereinafter be described.

Referring to FIG. 3, a sterilization apparatus 200 using a hydrogen peroxide solution, according to the second exemplary embodiment, includes a sterilization chamber 210.

The sterilization chamber 210 may be a vessel for receiving a target object to be sterilized, such as a medical instrument or a surgical instrument.

The sterilization chamber 210 may also include a vacuum pump 220, which is connected to one side of the sterilization chamber 210, and the vacuum pump 220 may form a vacuum state by exhausting the air from the sterilization chamber 210. A vacuum valve 221 capable of controlling an operation of the vacuum pump 220 is connected between the sterilization chamber 210 and the vacuum pump 220.

Referring further to FIG. 3, the sterilization apparatus 200 using a hydrogen peroxide solution, according to the second exemplary embodiment, also includes a vaporizer 230 (also referred to as an evaporator), which is connected to the other side of the sterilization chamber 210 and supplies a hydrogen peroxide vapor to the sterilization chamber 210, and a hydrogen peroxide supply device 250, which supplies hydrogen peroxide to the vaporizer 230.

A vaporization valve 231 may be provided between the sterilization chamber 210 and the vaporizer 230.

The sterilization apparatus 200 using a hydrogen peroxide solution, according to the first exemplary embodiment, also includes a collector 240 (also referred to as a collecting vaporizer), which has one side connected to the vaporizer 230 and the other side connected to the sterilization chamber 210 and concentrates the hydrogen peroxide supplied to the vaporizer 230.

A collection valve 241 may be provided between the sterilization chamber 110 and the collector 240.

A fumigation valve 251 may also be provided between the sterilization chamber 110 and the collector 240.

That is, the collection valve 241 and the fumigation valve 251 may be connected in parallel between the sterilization chamber 210 and the collector 240.

As described above, the vaporization valve 231 may be provided between the sterilization chamber 210 and the vaporizer 230. That is, the vaporization valve 231 may have one side connected to the sterilization chamber 210 and the other side connected in parallel between the vaporizer 230 and the collector 240.

Referring further to FIG. 3, the sterilization apparatus 200 using a hydrogen peroxide solution, according to the second exemplary embodiment, also includes a first connecting pipe 232, which connects the vaporizer 230 and the vaporization valve 231, and a second connecting pipe 233, which connects the vaporization valve 231 and the sterilization chamber 210.

The sterilization apparatus 200 using a hydrogen peroxide solution, according to the second exemplary embodiment, may also include a third connecting pipe 242, which connects the collector 240 and the collection valve 241, and a fourth connecting pipe 243, which connects the collection valve 241 and the sterilization chamber 210.

The sterilization apparatus 200 using a hydrogen peroxide solution, according to the second exemplary embodiment, may also include a fifth connecting pipe 252, which connects the collector 240 and the fumigation valve 251, and a sixth connecting pipe 253, which connects the fumigation valve 251 and the sterilization chamber 210.

FIG. 3 illustrates the fourth connecting pipe 243 as being connected to the sterilization chamber 210 so as for the collection valve 241 and the fumigation valve 251 to be connected in parallel between the sterilization chamber 210 and the collector 240, but the invention is not limited thereto. That is, alternatively, the fourth connecting pipe 243 may be connected to the sixth connecting pipe 253 so as for the collection valve 241 and the fumigation valve 251 to be connected in parallel between the sterilization chamber 210 and the collector 240.

The sterilization apparatus 200 using a hydrogen peroxide solution, according to the second exemplary embodiment, may also include a seventh connecting pipe 234, which connects the vaporizer 230 and the collector 240.

The vaporization valve 231, the collection valve 241, and the fumigation valve 251 may control the flow of a fluid in each of the first, second, third, fourth, fifth, and sixth connecting pipes 232, 233, 242, 243, 252, and 253 through an "open/close" operation. The "open/close" operation for the vaporization valve 231, the collection valve 241, and the fumigation valve 251 may be controlled by an additional controller.

As illustrated in FIG. 3, the fifth connecting pipe 252, which connects the collector 240 and the fumigation valve 251, and the sixth connecting pipe 253, which connects the fumigation valve 251 and the sterilization chamber 210, may have a larger inner diameter than the other connecting pipes. For example, in response to the other connecting pipes being ¼-inch pipes, the fifth and sixth connecting pipes 252 and 253 may be 1-inch pipes.

Although not specifically illustrated, temperature control means for controlling the temperature of the sterilization chamber 210, the vaporizer 230, and the collector 240 may be provided. The temperature control means may be a heater, which is obvious to a person skilled in the art to which the invention pertains, and thus, a detailed description of the temperature control means will be omitted.

The collector 240 may include cooling means as temperature control means thereof. The cooling means may use an appropriate cooling method such as a direct cooling method using a coolant or a thermoelectric device or an air cooling method using a heat exchanger.

A sterilization method using the sterilization apparatus according to the second exemplary embodiment will hereinafter be described.

The sterilization method using the sterilization apparatus according to the second exemplary embodiment will hereinafter be described with reference to the flowchart of FIG. 2, which illustrates a sterilization method using the sterilization apparatus according to the first exemplary embodiment, further to FIG. 3.

The sterilization method using the sterilization apparatus according to the second exemplary embodiment may be the same as the sterilization method using the sterilization apparatus according to the first exemplary embodiment except for a few aspects that will hereinafter be described.

Referring to FIG. 2, the sterilization method according to the present exemplary embodiment includes evacuating the sterilization chamber 210 (also referred to as a pasteurization chamber) and the vaporizer 230 to a vacuum (S110).

The sterilization chamber 210 and the vaporizer 130 may be evacuated by turning on the vacuum pump 220 and opening the vacuum valve 221.

S110, i.e., a step of evacuating the sterilization chamber and the vaporizer, may be continued until S160, which will be described later, begins, and may be completed in response to the sterilization chamber 210 reaching a predetermined pressure and a hydrogen peroxide liquid with moisture removed therefrom being collected in the collector.

To evacuate the vaporizer 230, the vaporization valve 231 between the sterilization chamber 210 and the vaporizer 230 may be opened to be in communication with the sterilization chamber currently being evacuated and thus to lower the pressure below atmospheric pressure, and may be closed in a subsequent step.

During the evacuation of the sterilization chamber 210 and the vaporizer 230, the sterilization chamber and the vaporizer may be maintained at a predetermined temperature by the aforementioned temperature control means.

Thereafter, the sterilization method includes introducing a hydrogen peroxide solution having a first concentration into the vaporizer 230 at a first temperature and a first pressure (S120).

The introduction of the hydrogen peroxide solution may be performed by the hydrogen peroxide supply device 250, which stores the hydrogen peroxide solution.

The first concentration may be 60 wt % or less.

The first temperature may range from 60° C. to 70° C., and the first pressure may be 800 mb or atmospheric pressure.

In S120, while the hydrogen peroxide solution having the first concentration is being introduced into the vaporizer 230, the vaporization valve 231, the collection valve 241, and the fumigation valve 251 may be closed, or may remain open depending on the type of the hydrogen peroxide supply device.

In S120, the sterilization chamber 210 may have a pressure of 600 mb to atmospheric pressure and a temperature of 45° C. to 55° C., and the collector 240 may have a pressure of 800 mb to atmospheric pressure and a temperature of 38° C. to 42° C.

Thereafter, the sterilization method according to the present exemplary embodiment includes obtaining a hydrogen peroxide solution having a second solution by vaporizing the hydrogen peroxide solution having the first concentration (S130).

That is, in response to the hydrogen peroxide solution having the first concentration being vaporized in the vaporizer 230 (i.e., water being removed from the hydrogen peroxide solution), the hydrogen peroxide solution having the second concentration is obtained.

The second concentration may be 75 wt % to 85 wt %. Accordingly, S130 may be a primary hydrogen peroxide solution concentration step for obtaining a hydrogen peroxide solution having a concentration of 75 wt % to 85 wt % by vaporizing a hydrogen peroxide solution having a concentration of 60 wt % or less.

In general, water evaporates more quickly than hydrogen peroxide at a given temperature and pressure because the vapor pressure of water is higher than the vapor pressure of hydrogen peroxide. Also, since the molecular weight of water is lower than the molecular weight of hydrogen peroxide, water diffuses more quickly than hydrogen peroxide.

Since water (or moisture) evaporates and diffuses more quickly than hydrogen peroxide at a given temperature and pressure, the water in a hydrogen peroxide solution also evaporates and diffuses into the air more quickly than the hydrogen peroxide in the hydrogen peroxide solution. Thus, the hydrogen peroxide solution having the second concentration may be obtained.

In S130, evaporated water may be exhausted by the vacuum pump via the sterilization chamber 210. Thus, in S130, the vacuum pump 220 may be turned on, and the vacuum valve 221 may be opened, thereby performing evacuation.

In S130, the vaporizer 330 may have a temperature of 55° C. to 65° C. and a pressure of 30 mb to 800 mb.

To exhaust evaporated water via the vacuum pump, the vaporization valve 231 may be opened.

While evaporated water is being exhausted through the sterilization chamber 210 and the vacuum pump, the sterilization chamber 210 may have a pressure of 10 mb to 600 mb and a temperature of 45° C. to 55° C., and the collector 240 may have a pressure of 20 mb to 500 mb and a temperature of 35° C. to 45° C.

Thereafter, the sterilization method according to the present exemplary embodiment includes injecting the hydrogen peroxide solution having the second concentration into the collector at a second temperature and a second pressure (S140).

To inject the hydrogen peroxide solution having the second concentration into the collector 240 at the second temperature and the second pressure, the vacuum pump 220 may be turned on, the vacuum valve 221 may be opened, the vaporization valve 231 and the fumigation valve 251 may be closed, and the collection valve 241 may be turned on.

The second temperature may be 35° C. to 42° C., and the second pressure may be 8 mb to 50 mb.

While the hydrogen peroxide solution having the second concentration is being transferred from the vaporizer 230 to the collector 240, the vaporizer 230 may have a pressure of 10 mb to 60 mb and a temperature of 55° C. to 60° C. The hydrogen peroxide solution having the second concentration may be transferred from the vaporizer 230 to the collector 240 via the seventh connecting pipe 234.

Even in S140, the evacuation of the sterilization chamber 210 is continued so that the sterilization chamber 210 may have a pressure of 1 mb to 10 mb and a temperature of 45° C. to 55° C.

Thereafter, the sterilization method according to the present exemplary embodiment includes condensing hydrogen peroxide vapor from the hydrogen peroxide solution having the second concentration in the collector, and exhausting water vapor from the hydrogen peroxide solution having the second concentration from the collector (S150).

The third concentration may be 90 wt % to 95 wt %. Accordingly, S150 may be a secondary hydrogen peroxide solution concentration step for obtaining a hydrogen peroxide solution having a concentration of 90 wt % to 95 wt % by vaporizing a hydrogen peroxide solution having a concentration of 75 wt % to 85 wt %.

In the present exemplary embodiment, S140, i.e., the step of injecting the hydrogen peroxide solution having the second concentration into the collector at the second temperature and the second pressure, and S150, i.e., a step of condensing hydrogen peroxide vapor from the hydrogen peroxide solution having the second concentration while exhausting water vapor from the hydrogen peroxide solution having the second concentration from the collector, may be sequentially performed, but the invention is not limited thereto. That is, alternatively, S140 and S150 may be performed at the same time.

In other words, the hydrogen peroxide solution having the second concentration may be injected into the collector at the second temperature and the second pressure, and at the same time, hydrogen peroxide vapor from the hydrogen peroxide solution having the second concentration may be condensed while exhausting water vapor from the hydrogen peroxide solution having the second concentration from the collector.

In S150, evaporated water may be exhausted via the vacuum pump. Thus, in S150, the vacuum pump 220 may be turned on, and the vacuum valve 221 may be opened so as to exhaust evaporated water. Also, to exhaust evaporated water through the vacuum pump, the collection valve 241 may be opened.

Thereafter, the sterilization method according to the present exemplary embodiment includes lowering the pressure of the sterilization chamber to a predetermined pressure and obtaining a hydrogen peroxide solution having a fourth concentration by concentrating the hydrogen peroxide solution having the third concentration (S160).

The predetermined pressure may be a pressure for sterilizing an object in the sterilization chamber. In response to the sterilant being hydrogen peroxide vapor, a vacuum state for facilitating the diffusion of hydrogen peroxide vapor needs to be established.

Thus, the predetermined pressure may be 0.5 mb to 1.3 mb, and the temperature of the sterilization chamber 110 may be 45° C. to 55° C.

The fourth concentration may be 95 wt % or higher. Accordingly, S160 may be a tertiary hydrogen peroxide solution concentration step for obtaining a hydrogen peroxide solution having a concentration of 95 wt % or higher by vaporizing a hydrogen peroxide solution having a concentration of 90 wt % to 95 wt %.

In S160, evaporated water may be exhausted via the vacuum pump. Thus, in S160, the vacuum pump 220 may be turned on, and the vacuum valve 221 may be opened so as to exhaust evaporated water.

In S160, the collection valve 141 may be repeatedly opened and closed, which has been described above and thus will not be described again.

In S160, the vaporization valve 231 and the fumigation valve 251 may be closed.

In S160, the collector 240 may have a pressure of 5 mb to 10 mb and a temperature of 35° C. to 40° C., and the vaporizer 230 may have a pressure of 7 mb to 10 mb and a temperature of 60° C. to 70° C.

Thereafter, the sterilization method according to the present exemplary embodiment includes injecting hydrogen peroxide vapor of the hydrogen peroxide solution having the fourth concentration into the sterilization chamber and sterilizing the target object in the sterilization chamber (S170).

In S170, to inject the hydrogen peroxide vapor of the hydrogen peroxide solution having the fourth concentration from the collector 240 into the sterilization chamber 210, the fumigation valve 251 may be opened.

That is, hydrogen peroxide vapor may be transferred from the collector 240 to the sterilization chamber 210 via the fifth and sixth connecting pipes 252 and 253.

As already mentioned above, the fifth connecting pipe 252, which connects the collector 240 and the fumigation valve 251, and the sixth connecting pipe 253, which connects the fumigation valve 251 and the sterilization chamber 210, may have a larger inner diameter than the other connecting pipes, particularly, the seventh connecting pipe 234. For example, in response to the seventh connecting pipe 234 being a ¼-inch pipe, the fifth and sixth connecting pipes 252 and 253 may be 1-inch pipes, which has been described above and thus will not be described again.

In response to the hydrogen peroxide solution having the fourth concentration being injected into the sterilization chamber 210, hydrogen peroxide may be diffused into the sterilization chamber in a gaseous state, and the heating rate of the collector 240 may be controlled such that the vaporization of the hydrogen peroxide may be almost complete before the temperature of the collector 240 reaches the temperature of the sterilization chamber, which has already been described above and will not be described again.

In S170, the sterilization chamber 210 may have a pressure of 0.5 mb to 15 mb and a temperature of 45° C. to 55° C.

Also, the collector 240 have a pressure of 0.5 mb to 15 mb and a temperature of 30° C. to 70° C., and the vaporizer 230 may have a pressure of 0.5 mb to 15 mb and a temperature of 60° C. to 70° C. or higher.

The pressure and temperature conditions in each of the steps of the sterilization method according to the present exemplary embodiment are as shown in Table 7 below.

TABLE 7

| Classification | Vaporizer | | Collector | | Sterilization chamber | |
|---|---|---|---|---|---|---|
| | Pressure (mb) | Temperature (° C.) | Pressure (mb) | Temperature (° C.) | Pressure (mb) | Temperature (° C.) |
| S120 | 800~Atmospheric Pressure | 60~70 | 800~Atmospheric Pressure | 38~42 | 600~Atmospheric Pressure | 45~55 |
| S130 | 30~800 | 55~65 | 20~500 | 35~40 | 10~600 | 45~55 |
| S140, S150 | 10~60 | 55~60 | 8~50 | 35~42 | 1~10 | 45~55 |
| S160 | 7~10 | 60~70 | 5~10 | 35~40 | 0.5~1.3 | 45~55 |
| S170 | 0.5~15 | 60~70 | 0.5~15 | 30~70 | 0.5~15 | 45~55 |

The states of the vacuum pump and the valves in each of the steps of the sterilization method according to the present exemplary embodiment are as shown in Table 8 below.

TABLE 8

| Classification | Vacuum Pump | Vacuum Valve | Vaporization Valve | Collection Valve | Fumigation Valve |
|---|---|---|---|---|---|
| S120 | On or off | Open or Close | Close | Close | Close |
| S130 | On | Open | Open | Open or close | Close |
| S140, S150 | On | Open | Close | Open | Close |
| S160 | On | Open | Close | Repeatedly open and close | Close |
| S170 | Off | Close | Open or Close | Open or close | Open |

The exemplary embodiments of the invention have been described with reference to the accompanying drawings. However, those skilled in the art will appreciate that many variations and modifications can be made to the disclosed embodiments without substantially departing from the principles of the invention. Therefore, the disclosed embodiments of the invention are used in a generic and descriptive sense only and not for purposes of limitation.

DESCRIPTION OF REFERENCE NUMERALS

| | |
|---|---|
| 100, 200: Sterilization apparatus | 110, 210: Sterilization chamber |
| 120, 220: Vacuum pump | 130, 230: Vaporizer |
| 140, 240: Collector | 131, 231: Vaporization valve |
| 141, 241: Collection valve | 251: Fumigation valve |

What is claimed is:

1. A sterilization apparatus, comprising:
a sterilization chamber;
a vacuum pump connected to one side of the sterilization chamber;
a vaporizer connected to another side of the sterilization chamber;
a collector having one side connected to the vaporizer and the other side connected to the sterilization chamber;
a vaporization valve disposed between the sterilization chamber and the collector,
wherein the vaporization valve is also disposed between the sterilization chamber and the vaporizer;
a collection valve disposed between the sterilization chamber and the collector,
wherein the vaporization valve and the collection valve are connected in parallel between the sterilization chamber and the collector;
a first connecting pipe connecting the collector and the vaporization valve;
a second connecting pipe connecting the vaporization valve and the sterilization chamber;
a third connecting pipe connecting the collector and the collection valve;
a fourth connecting pipe connecting the collection valve and the sterilization chamber; and
a fifth connecting pipe connecting the vaporizer and the vaporization valve.

2. The sterilization apparatus of claim 1,
wherein the vaporization valve has one side connected to the sterilization chamber; and
wherein the other side of the vaporization valve is connected to the vaporizer and is connected to the collector.

3. The sterilization apparatus of claim 1, wherein the first and second connecting pipes have a larger inner diameter than the third or fourth connecting pipe and the fifth connecting pipe.

4. A sterilization apparatus comprising:
a sterilization chamber;
a vacuum pump connected to one side of the sterilization chamber;
a vaporizer connected to another side of the sterilization chamber;
a collector having one side connected to the vaporizer and the other side connected to the sterilization chamber;
a collection valve and a fumigation valve disposed between the sterilization chamber and the collector,
wherein the collection valve and the fumigation valve are connected in parallel between the sterilization chamber and the collector;
a vaporization valve disposed between the sterilization chamber and the vaporizer,
wherein the vaporization valve has one side connected to the sterilization chamber, and
wherein the other side of the vaporization valve is connected to the vaporizer and the vaporizer is connected to the collector;
a first connecting pipe connecting the vaporizer and the vaporization valve;
a second connecting pipe connecting the vaporization valve and the sterilization chamber;
a third connecting pipe connecting the collector and the collection valve;
a fourth connecting pipe connecting the collection valve and the sterilization chamber;
a fifth connecting pipe connecting the collector and the fumigation valve;
a sixth connecting pipe connecting the fumigation valve and the sterilization chamber; and
a seventh connecting pipe connecting the vaporizer and the collector.

5. The sterilization apparatus of claim 4, wherein the fifth and sixth connecting pipes have a larger inner diameter than the first or second connecting pipe, the third or fourth connecting pipe, and the seventh connecting pipe.

* * * * *